(12) United States Patent
Gertitschke (10) Patent No.: US 9,063,096 B2
(45) Date of Patent: Jun. 23, 2015

(54) DEVICE FOR INSPECTING SMALL PHARMACEUTICAL PRODUCTS

(75) Inventor: Detlev Gertitschke, Laupheim (DE)

(73) Assignee: Uhlmann Pac-Systeme GmbH & Co. KG, Laupheim (DE)

( * ) Notice: Subject to any disclaimer, the term of this patent is extended or adjusted under 35 U.S.C. 154(b) by 554 days.

(21) Appl. No.: 13/416,507

(22) Filed: Mar. 9, 2012

(65) Prior Publication Data

US 2012/0241617 A1    Sep. 27, 2012

(30) Foreign Application Priority Data

Mar. 25, 2011   (EP) ..................................... 11159845

(51) Int. Cl.
| | | |
|---|---|---|
| *G01N 21/15* | (2006.01) | |
| *G01N 21/95* | (2006.01) | |
| *A61J 7/02* | (2006.01) | |
| *B07C 5/34* | (2006.01) | |
| *B07C 5/36* | (2006.01) | |
| *G01N 21/3563* | (2014.01) | |
| *G01N 21/85* | (2006.01) | |
| *G01N 25/72* | (2006.01) | |
| *G01N 33/15* | (2006.01) | |
| *B65B 37/04* | (2006.01) | |
| *B65B 57/14* | (2006.01) | |
| *B65B 5/10* | (2006.01) | |

(52) U.S. Cl.
CPC .............. *G01N 21/9508* (2013.01); *A61J 7/02* (2013.01); *B07C 5/34* (2013.01); *B07C 5/366* (2013.01); *G01N 21/3563* (2013.01); *G01N 21/85* (2013.01); *G01N 25/72* (2013.01); *G01N 33/15* (2013.01); *G01N 2021/151* (2013.01); *B65B 37/04* (2013.01); *B65B 57/14* (2013.01); *B65B 5/103* (2013.01)

(58) Field of Classification Search
CPC ........................... G01N 21/9508; B65B 5/103
USPC ..................................................... 250/339.03
See application file for complete search history.

(56) References Cited

U.S. PATENT DOCUMENTS

| | | | |
|---|---|---|---|
| 5,027,938 A | 7/1991 | Haggarty et al. | |
| 5,638,417 A * | 6/1997 | Boyer et al. | ...................... 377/7 |
| 5,884,806 A | 3/1999 | Boyer et al. | |
| 6,324,253 B1 | 11/2001 | Yuyama et al. | |
| 6,541,271 B1 * | 4/2003 | McFarland et al. | ............. 506/12 |
| 2004/0003611 A1 * | 1/2004 | Walter | ........................... 62/190 |
| 2011/0174331 A1 * | 7/2011 | Kim | ............................. 132/229 |
| 2012/0012750 A1 * | 1/2012 | Sinbar et al. | ............. 250/339.03 |

FOREIGN PATENT DOCUMENTS

| | | |
|---|---|---|
| DE | 4312550 C1 | 9/1994 |
| WO | WO 2009/019698 A2 | 2/2009 |

OTHER PUBLICATIONS

EP Search Report for EP 11159845 dated Aug. 4, 2011.

* cited by examiner

*Primary Examiner* — Casey Bryant
(74) *Attorney, Agent, or Firm* — Brinks Gilson & Lione (57) ABSTRACT

The device for inspecting separately conveyed tablets or capsules has a guide device for guiding the separately conveyed tablets or capsules, which defines a predetermined tablet pathway, and a heating element designed as a hotplate, which is arranged in an area of the guide device. The device further has an IR sensor for detecting radiation in an infrared range arranged opposite the heating element such that the tablet pathway passes between the heating element and the IR sensor, and an evaluation unit connected to the IR sensor and adapted to compare actual measurement values of the IR sensor with at least one predetermined nominal measurement value.

20 Claims, 10 Drawing Sheets

DEVICE FOR INSPECTING SMALL PHARMACEUTICAL PRODUCTS

RELATED APPLICATIONS

The present patent document claims the benefit of priority to European Patent Application No. EP 11159845.4, filed Mar. 25, 2011, and entitled "DEVICE FOR INSPECTING SMALL PHARMACEUTICAL PRODUCTS" the entire contents of each of which are incorporated herein by reference.

FIELD AND BACKGROUND

The present invention relates to a device for inspecting small pharmaceutical products such as tablets or capsules.

Important functions which are to be performed when bottles or other containers are being filled with tablets or capsules are to count the tablets or capsules and to sort out the defective ones. Commercially available systems work with different technologies.

Color cameras can detect incorrectly colored or broken tablets or capsules by appropriate evaluation of the images. Because of the continuous movement of the tablets or capsules past the camera, however, highly complex evaluation software is required. Considerable effort is also required to provide illumination sufficient to achieve sharply focused images.

Capacitive sensors can be used to calculate the weights of the tablets or capsules passing by them without the need for direct contact. From this information it is possible to determine whether or not the tablets or capsules are intact. Capacitive sensors are sensitive to vibrations, however, and also to interfering electrical fields and to the moisture content of the tablets or capsules.

BRIEF SUMMARY

It is an object of the present invention to provide a device for inspecting tablets or capsules which is highly robust and simple in design and which can be used for products of different types and formats.

According to an aspect of the invention, the device for inspecting separately conveyed tablets or capsules comprises:
a guide device for guiding the separately conveyed tablets or capsules, which defines a predetermined tablet pathway;
a heating element designed as a hotplate, which is arranged in an area of the guide device;
an IR sensor for detecting radiation in an infrared range arranged opposite the heating element such that the tablet pathway passes between the heating element and the IR sensor; and
an evaluation unit connected to the IR sensor and adapted to compare actual measurement values of the IR sensor with at least one predetermined nominal measurement value.

With this arrangement it is possible to inspect separately conveyed tablets or capsules quickly and reliably with respect to their color, shape, and intactness. The device is extremely resistant to external influences and can be used for tablets and capsules of different shapes and sizes.

The heating element is preferably isolated from or arranged separately from the guide device. This increases the reliability of the device.

To optimize the measurement results, the temperature of the heating element is preferably adjustable.

The heating element is preferably made of metal, and even more preferably of aluminum, in order to produce a uniform temperature and to allow easy heating of the heating element.

Because smooth metals usually have a relatively low emission value, the heating element preferably comprises a nonmetallic coating with a high emission value on the surface facing the tablet pathway. This offers the additional advantage that the emission value of nonmetals depends hardly at all on temperature and wavelength.

To prevent damage to the tablets or capsules which might be caused by the high temperature of the heating element, an IR-permeable plate, preferably made of IR-permeable glass, can be arranged between the heating element and the tablet pathway.

For precise adjustment of the field of view of the IR sensor and for an adaptation of the device to inspect tablets of different sizes, a field-of-view diaphragm is preferably arranged between the heating element and the tablet pathway.

The IR sensor preferably comprises an ancillary lens for adjusting the size of the field of view.

The distance between the IR sensor and the field of view is preferably in the range of 20 to 50 mm, depending on the shape of the product.

The associated field of view comprises a variable size in the range of between 25 and 1,000 $mm^2$, depending on the shape and type of product.

The actual measurement values measured by the IR sensor are usually temperature values. These temperature values are determined by the IR sensor preferably on the basis of the IR radiation received from the entire area of the field of view, and they therefore represent average temperature values.

In a preferred embodiment, the IR sensor measures a continuous temperature curve, which can be compared according to predetermined criteria with a corresponding nominal temperature curve.

In a preferred embodiment, the guide device is a vibrating trough. The guide device could also be designed as a nonvibrating or vibrating product chute.

BRIEF DESCRIPTION OF THE DRAWINGS

Additional advantages and features of the present invention can be derived from the following description, which makes reference to the drawings.

DETAILED DESCRIPTION OF SPECIFIC EMBODIMENTS

Figure 1:
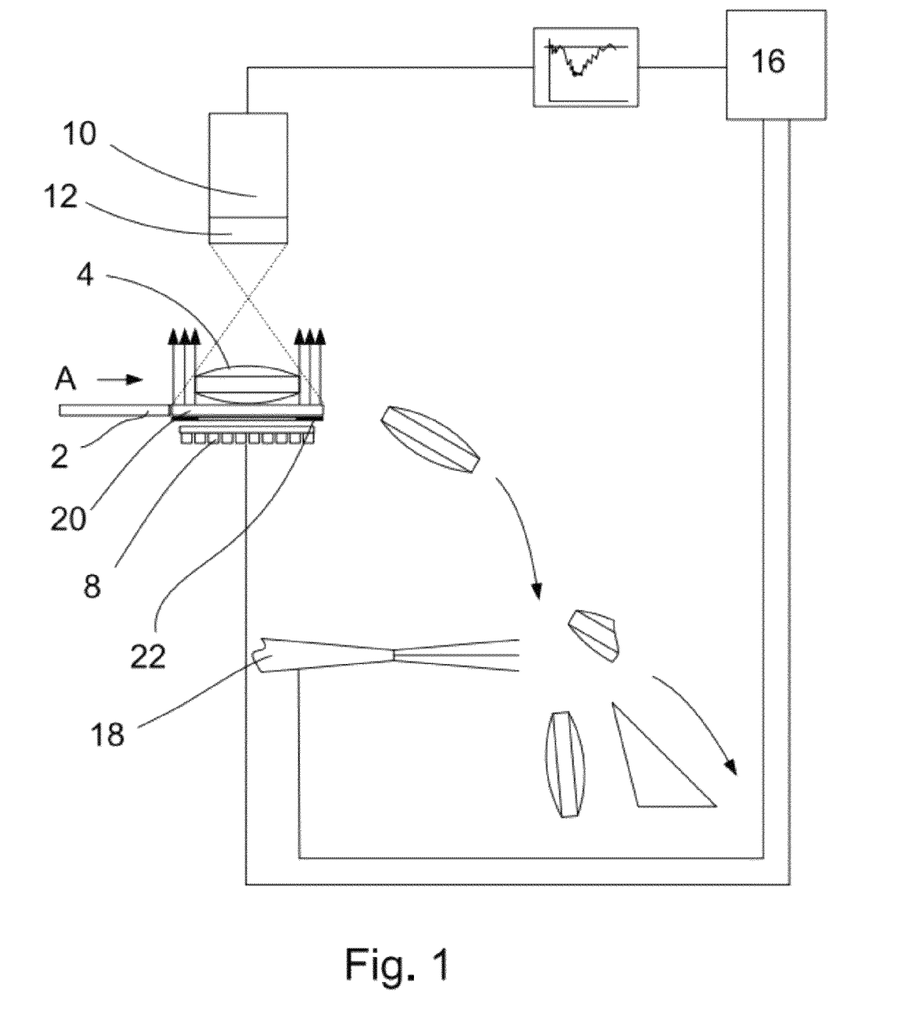
FIG. 1 is a schematic diagram of all the components of a device for inspecting small pharmaceutical products according to the invention.
Figure 2:
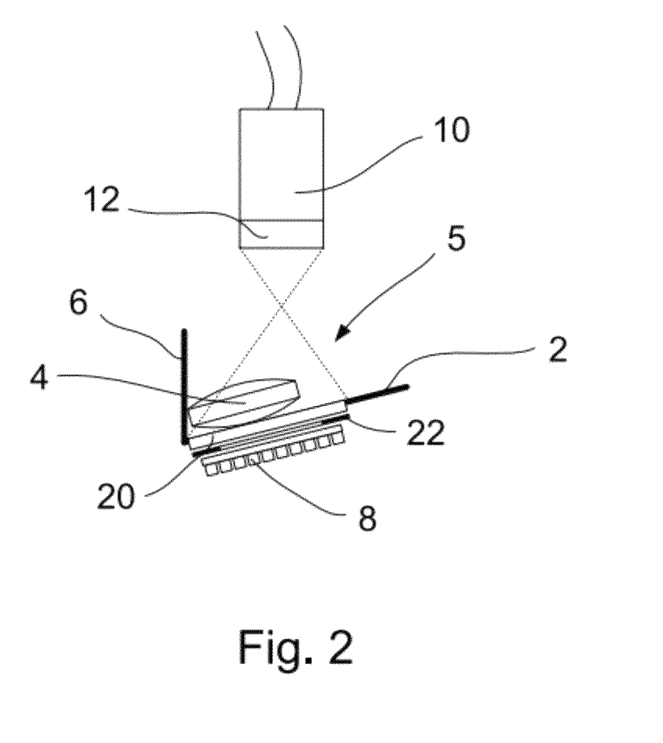
FIG. 2 is a schematic diagram of the front of part of a first embodiment of the device for inspecting small pharmaceutical products according to the invention.
Figure 3:
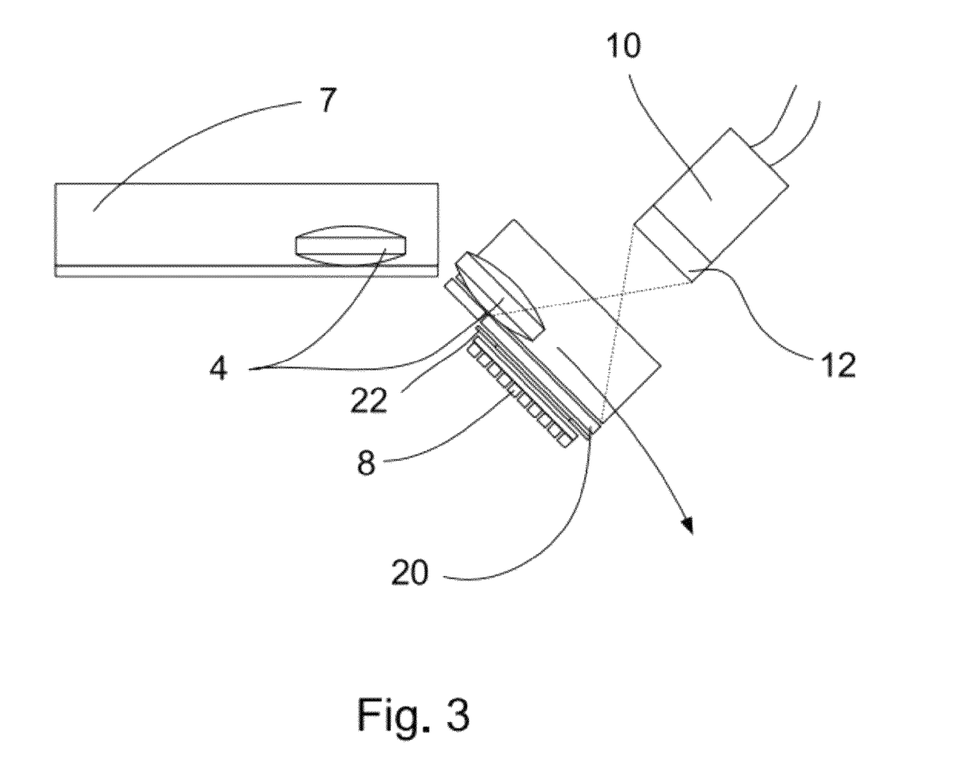
FIG. 3 is a schematic diagram of the side of part of a second embodiment of the device for inspecting small pharmaceutical products according to the invention.

FIG. 1 is a schematic diagram of the components of a device for inspecting small pharmaceutical products (tablets or capsules) according to the invention. For the sake of simplicity, the term "tablet" is used in the following in place of the term "small pharmaceutical product". The device comprises a guide device 2 for separately conveyed tablets 4, which defines a predetermined tablet pathway A, along which the tablets 4 are conveyed forward. The guide device 2 can be designed as a vibrating trough, as shown in FIG. 2. In this case, the guide device 2 can comprise V-shaped grooves 5, for example, with a more-or-less vertical wall section 6 to ensure the exact guidance of the tablets 4, as shown in FIG. 2. Alternatively, the guide device 2 can be designed as a vibrating or non-vibrating product chute, to which the products are supplied one by one by a transport device 7 such as a vibrating trough, as shown in FIG. 3.

The device for inspecting tablets comprises a heating element 8, which is heated uniformly to a predetermined temperature. The temperature of the heating element is preferably 40-80° C., and even more preferably 50-70° C. The heating element 8 preferably consists of a metal with good thermal conductivity such as aluminum and is heated directly by a resistance wire. Alternatively, the heating element 8 can also be heated without contact by means of induction or infrared radiation.

The heating element 8 can be set to a temperature suitable for the application and is preferably supported in a manner isolated from the guide device 2 so that it will not be subjected to vibrations. In the exemplary embodiments shown here, the heating element 8 is designed as a hotplate. The important point is that the heating element 8 should have the most uniform possible temperature and thus emit the most uniform possible infrared (IR) radiation over its surface toward the tablet pathway A. The heating element 8 is arranged in all cases in the area of the guide device 2.

According to the invention, the IR radiation of the heating element 8 should be as intense as possible. Because metals have a relatively low emission value $\epsilon$, the surface of the heating element 8 facing the tablet pathway A is thus preferably coated with a nonmetallic coating with a high emission value. The coating can consist of matte-black, heat-resistant lacquer, for example, and should preferably have an emission value $\epsilon$ of >0.9, and more preferably of >0.95.

An infrared sensor (IR sensor) 10 is set up opposite the heating element 8 to detect radiation in the infrared range, wherein the tablet pathway A passes between the heating element 8 and the IR sensor 10. The IR sensor 10 preferably comprises an ancillary lens 12, which makes it possible to adjust the size of a two-dimensional field of view 14 along the tablet pathway A (see especially FIG. 4). In preferred embodiments, the IR sensor 10 comprises a distance from the field of view 14 of 20-50 mm, and the field of view 14 can comprise a variable size of 25-1,000 mm$^2$, depending on the application in question. The IR sensor 10 can be equipped with dust protection and a compressed-air cleaning device (not shown). The IR sensor 10 preferably has an extremely fast response time of only a few milliseconds. If necessary, the area between the IR sensor 10 and the field of view 14 can be surrounded by a housing to block out foreign radiation. Experiments have shown, however, that the function of the device suffers almost no impairment even when not protected by an additional housing.

The background for the measurements performed by the IR sensor 10 is that every body emits IR radiation of varying intensity and wavelength depending on its temperature and material composition. The IR sensor 10 is able to record the actual values of the IR radiation being emitted over the entire area of the field of view 14 in the direction of the IR sensor 10 and to determine an average temperature from that set of data at any desired point in time.

Figure 4:
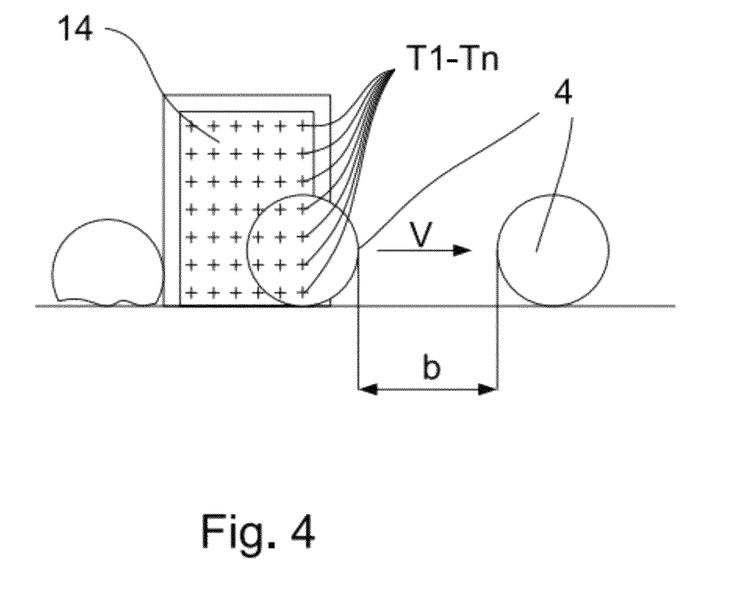
FIG. 4 is a schematic diagram of the measurement principle of the device for inspecting small pharmaceutical products according to the invention.

As can be seen in FIG. 4, an infinite number of emission points at a predetermined temperature $T_1$-$T_n$ are present in the field of view 14 at every moment in time. When a "cold" tablet 4 (usually at 20-22° C.) now travels through the field of view 14, the heating element 8 will be partially covered by the tablet 4, and a significantly different actual measurement value will be recorded by the IR sensor 10.

An evaluation unit 16, shown in FIG. 1, is set up to compare the actual measurement values of the IR sensor 10 with at least one predetermined nominal measurement value. This comparison will be discussed further below in more detail.

The evaluation unit 16 can also arrange to have tablets 4 which have been classified as "bad" sorted out by a sorting device 18, shown by way of example in FIG. 1 as an air-blast nozzle.

Because of the considerable heat generated by the heating element 8, it is advantageous that an IR-permeable plate 20 with the lowest possible thermal conductivity is arranged between the heating element 8 and the tablet pathway A. This IR-permeable plate 20 can consist of, for example, IR-permeable glass. The IR-permeable plate 20 can, as shown in FIGS. 2 and 3, be part of the guide device 2 for the tablets 4 in such a way that the tablets 4 are moved directly over the IR-permeable plate 20 or slide directly on it.

For a precise adjustment of the field of view 14, it is advantageous that a field-of-view diaphragm 22 is arranged between the heating element 8 and the tablet pathway A, and even more preferably between the heating element 8 and the IR-permeable plate 20. Adjusting the field-of-view diaphragm 22 makes it possible to optimize the device for tablets 4 to be inspected of various sizes and shapes, if necessary.

The course of the inspection measurement will now be described in summary fashion with reference to FIGS. 1 and 4. The tablets 4 are conveyed forward along the guide device 2 or slide along it at a preferably more-or-less uniform conveying speed v and preferably also with approximately the same distance b between adjacent tablets and at a nearly constant temperature (preferably in the range of 20-22° C.). Thus the tablets 4 also travel through the field of view 14, which can be defined by the field-of-view diaphragm 22, if desired. When the tablets 4 pass through the field of view 14, the cold tablet 4 casts a shadow on part of the heating element 8. This is detected by the IR sensor 10, and the actual measurement result of the IR sensor 10 is compared in the evaluation unit 16 with a learned nominal measurement value. If there is a significant difference between the actual measurement value and the nominal one, an error signal is triggered, which leads to the actuation of the sorting-out device 18.

Figure 5:
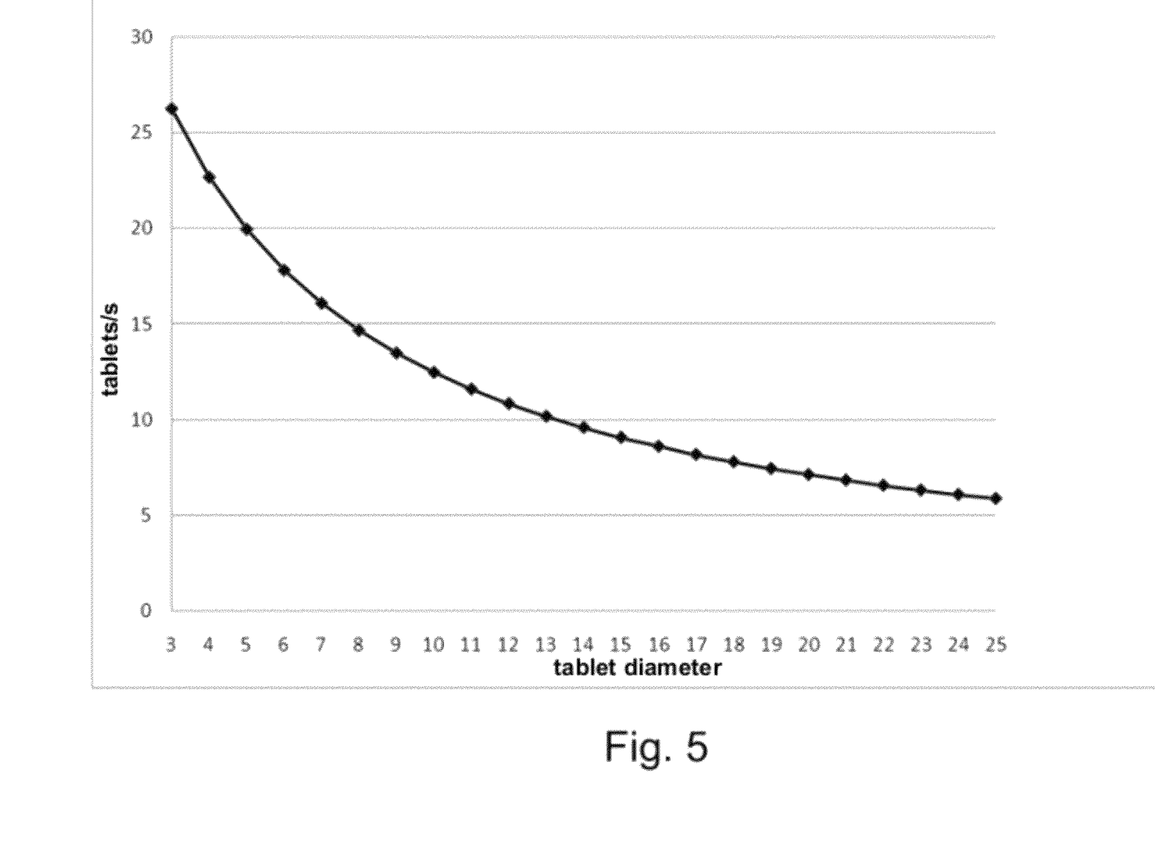
FIG. 5 is a graph, which represents the relationship between the tablet diameter and the number of tablets inspected per second.

FIG. 5 shows by way of example the achievable throughput at a tablet speed v of, for example, 0.17 m/s for tablets of various sizes. It can be seen that, as the tablet diameter increases, the number of tablets 4 inspected per second decreases.

Figure 6:
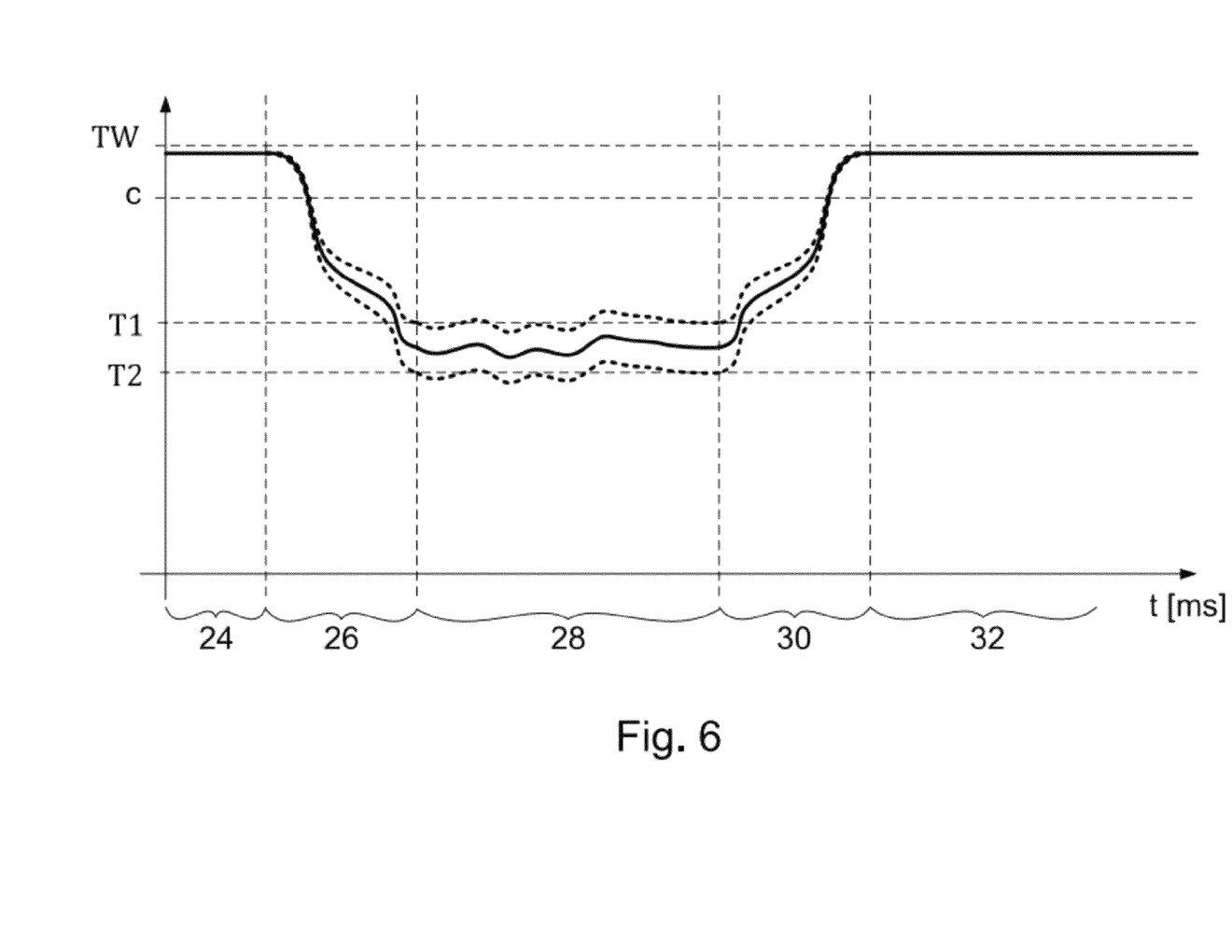
FIG. 6 is a schematic diagram of a possible curve of the actual measurement values of the IR sensor.

FIG. 6 shows by way of example a signal curve to be expected for the actual measurement values of the IR sensor 10. First, the IR sensor 10 measures a signal which moves along a plateau 24, corresponding to the constant reference temperature TW of the heating element 8. When the tablet 4 enters the area of the field of view 14, the signal intensity of the IR radiation detected by the IR sensor 10 decreases in correspondence with the increasing coverage of the heating element 8 by the tablet 4 (area 26). As soon as the tablet 4 is completely within the field of view 14, the signal of the IR sensor 10 reaches a minimum or lower plateau 28. As soon as the tablet 4 starts to leave the field of view 14 again, the signal received by the IR sensor 10 begins to increase (area 30). The actual measurement value of the IR sensor 10 then reaches a plateau 32 again, which corresponds to the constant temperature of the heating element 8.

The actual measurement values of the IR sensor 10 can be recorded and evaluated in various ways. As a rule, evaluation is performed only during the time (area 28) that the tablet 4 is located completely within the field of view 14. A predetermined change in temperature upon arrival of the tablet 4 in the field of view 14 can be used as a triggering signal c, possibly with a predetermined time delay. This triggering signal can also be used to provide a counting function and, with a predetermined time delay, to actuate the sorting-out function.

As previously explained, the measurement result is a temperature value averaged over the entire surface of the field of view 14. Based on graphs of the type shown in FIG. 6, it is now possible to use, for example, the minimum signal level in the area 28 or the integral under the signal in part of the area 28 or in the entire area 28 as a decision criterion. When the actual measurement values are outside certain tolerance values T1, T2, which can be preset, the corresponding tablet 4 is sorted out. The nominal measurement values of the reference signal can be generated by means of test runs with a good tablet 4 or with a sequence of good tablets 4. Corresponding nominal measurement values could also be learned by the use of software.

The measurement is a relative measurement, which means that any temperature drifts have no effect. As a result, it is also possible to compensate for a small amount of dust on the IR sensor 10. By re-adjusting the temperature of the heating element 8, furthermore, the temperature difference between the tablet 4 and the heating element 8 can be kept constant, when, for example, the temperatures of tablets 4 or of the guide device 2 change during continuous operation.

To ensure that tablets of a different color, tablets of a different shape, and broken tablets can be reliably detected, the ratio of the surface area of the field of view 14 to the surface area of the tablet 4 should be in the range below 3:1. The field of view 14, however, should always be at least as large as the tablet 4 itself.

Figure 7:
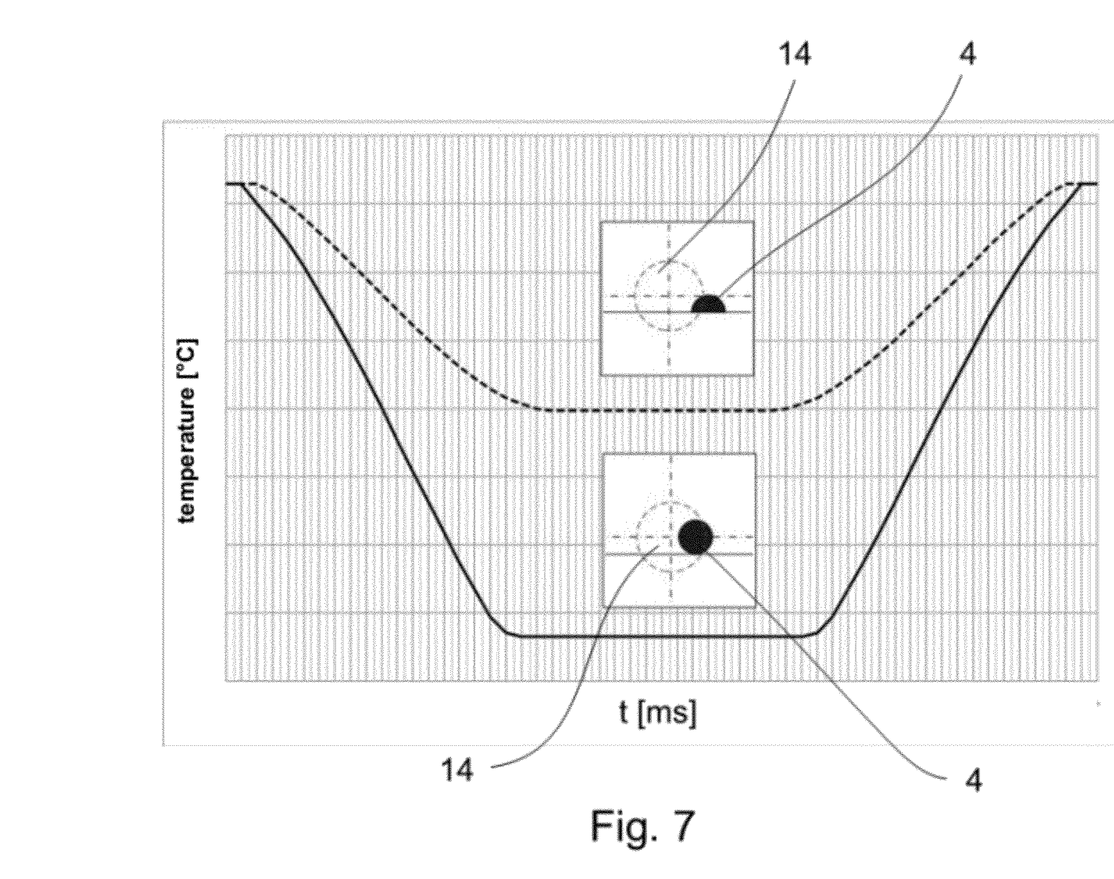
FIGS. 7-9 are schematic graphs, which show measurement results of the IR sensor which are to be expected theoretically under different sets of conditions.
Figure 8:
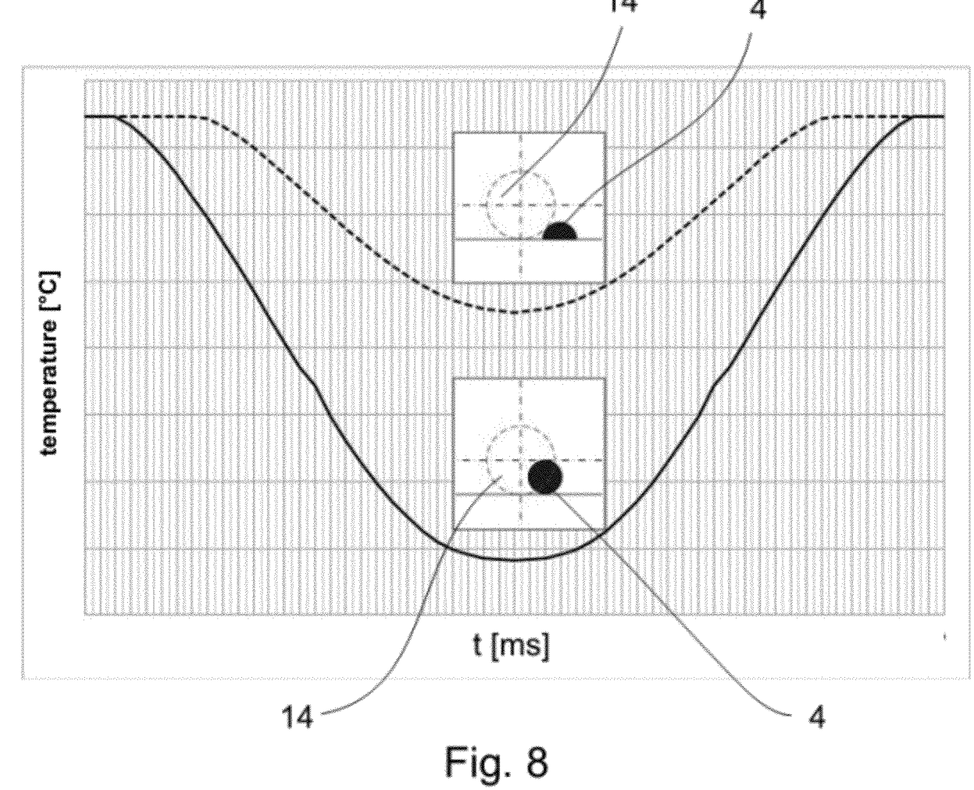
Figure 9:
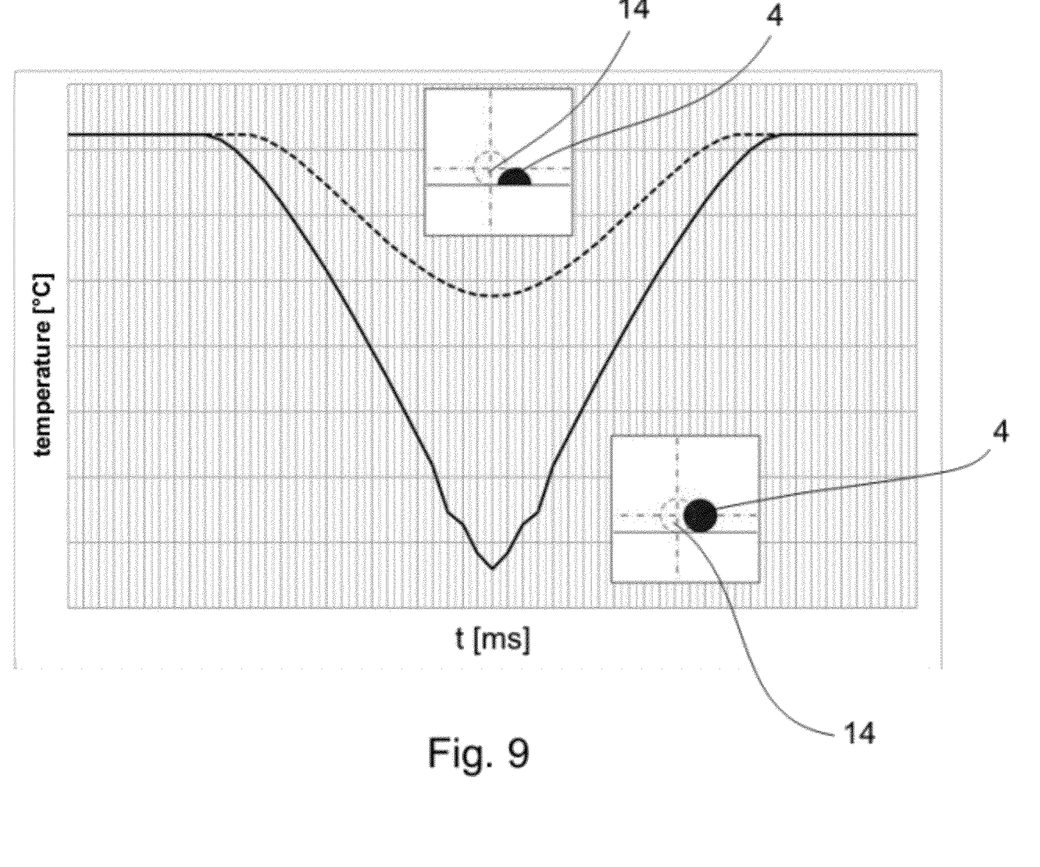

FIGS. 7-9 show a few theoretical measurement curves of the IR sensor 10 for different configurations. As can be seen on the right side of the diagrams, the field of view 14 in FIGS. 7 and 8 is approximately 2.5 times larger than the surface area of the tablet 4. The solid line shows the theoretical course of the actual measurement values of the IR sensor 10 to be expected for an intact tablet 4, whereas the curve in broken line shows the actual values to be expected theoretically for half a tablet. The same is true for FIG. 8, where the tablets 4 travel through only the lower part of the field of view 14, and thus the length of the minimum of the temperature measurement curve is reduced. FIG. 9 shows the situation in which the field of view 14 is equal to the size of the tablet 4. Here we can see that the difference between the signal height for an intact tablet and that for half a tablet is greater than in the two preceding diagrams, although the curves also comprise relatively sharp minima.

Figure 10:
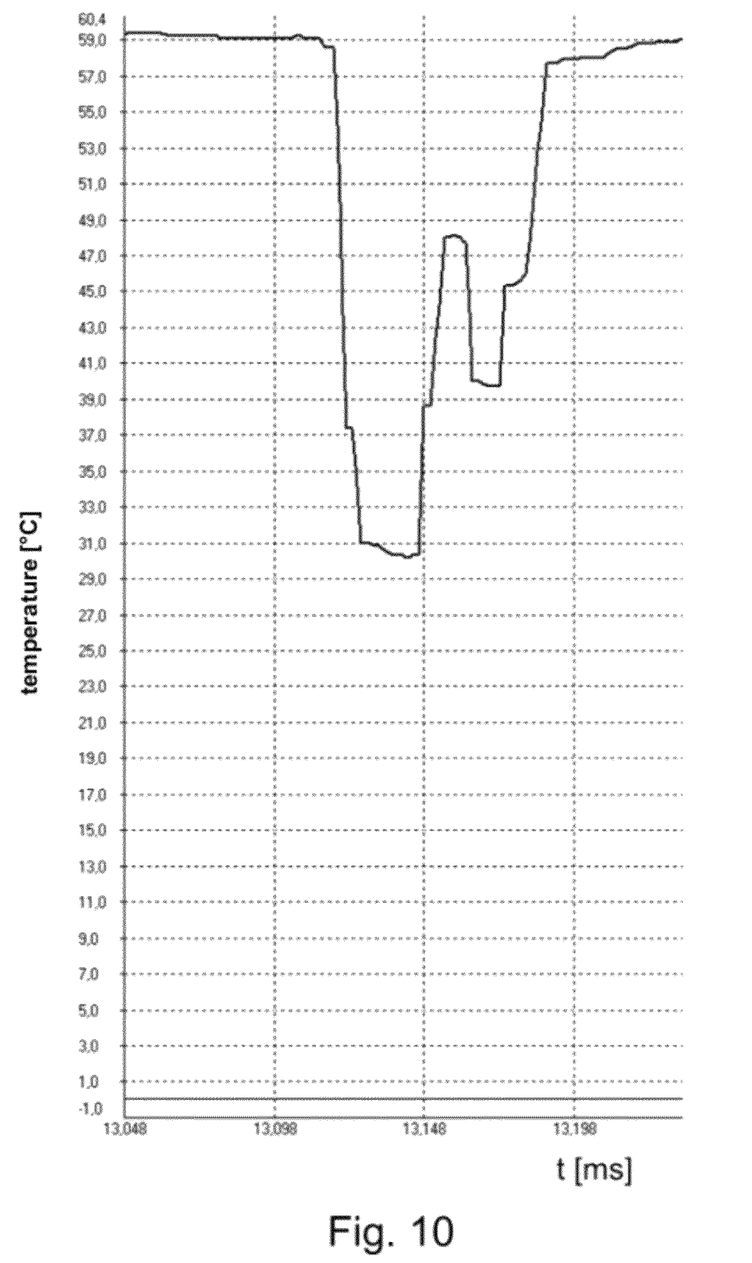
FIG. 10 is a graph of actual measurement values of the IR sensor actually recorded for an intact tablet and a broken tablet.

FIG. 10 shows an actually measured temperature curve, wherein the first minimum characterizes an intact tablet 4, and wherein the second minimum characterizes a broken half-tablet 4. The difference between the deflections is obvious, with respect to both the signal level and the length of the minimum-value plateau.

In the embodiment of the guide device 2 as a vibrating trough (FIG. 2), the speed of the tablets 4 along the tablet pathway A can be set to remain relatively constant, which makes the inspection easier, whereas the speed of the tablets 4 along the tablet pathway A in the case of the embodiment according to FIG. 3 increases somewhat as the tablets pass along the product chute. Conversely, in the case of the embodiment according to FIG. 2, the vibrations of the vibrating trough cause the tablets 4 to wobble, which can lead in turn to certain measurement inaccuracies. This is ruled out in the case of the embodiment according to FIG. 3 showing a non-vibrating chute. All of the variations described above, however, have hardly any effect on the results of the inventive measurement, thanks to the robust design, and they can also be taken into consideration when setting the limit values of the tolerances for "good" tablets.

With the device according to the invention, most of the broken tablets, tablets of the wrong color, and tablets of the wrong shape can be detected. It is also suitable for counting the tablets. In the case of multi-track guide devices 2, a separate IR sensor 10 should be provided for each track of the guide device 2.

It is thus possible to inspect the tablets 4 reliably and robustly and also to count them immediately before they are loaded into the associated bottles or containers.

The invention claimed is:

1. A device for inspecting separately conveyed tablets or capsules comprising:
 a guide device for guiding the separately conveyed tablets or capsules, which defines a predetermined tablet pathway;
 a hotplate, arranged in an area of the guide device;
 an IR sensor for detecting radiation in an infrared range arranged opposite the hotplate such that the tablet pathway passes between the hotplate and the IR sensor, wherein the tablets or capsules are cooler than the hot plate during detection by the IR sensor; and
 an evaluation unit connected to the IR sensor and adapted to compare actual measurement values of the IR sensor with at least one predetermined nominal measurement value.

2. The device of claim 1 wherein the hotplate is isolated from the guide device.

3. The device of claim 1 wherein the hotplate is adjustable with respect to a temperature of the heating element.

4. The device of claim 1 wherein the hotplate is made of metal.

5. The device of claim 4 wherein the hotplate is made of aluminum.

6. The device of claim 1 wherein, on a surface facing the tablet pathway, the hotplate is coated with a nonmetallic coating having a high emission value.

7. The device of claim 1 wherein an IR-permeable plate is arranged between the hotplate and the tablet pathway to reduce transmission of heat from the hotplate to the tablets or capsules.

8. The device of claim 7 wherein the IR-permeable plate is made of IR-permeable glass.

9. The device of claim 1 wherein a field-of-view diaphragm is arranged between the hotplate and the tablet pathway.

10. The device of claim 1 wherein the IR sensor comprises an ancillary lens for adjusting a size of a field of view of the IR sensor.

11. The device of claim 1 wherein a distance between the IR sensor and a desired field of view of the IR sensor is 20 to 50 mm.

12. The device of claim 1 wherein a desired field of view of the IR sensor comprises a variable size in the range of between 25 and 1,000 mm$^2$.

13. The device of claim 1 wherein the actual measurement values of the IR sensor are temperature measurement values.

14. The device of claim 13 wherein the actual measurement values of the IR sensor form a temperature curve.

15. The device of claim 1 wherein the guide device is a vibrating trough.

16. The device of claim 1 wherein the guide device is a product chute.

17. The device of claim 1 wherein the IR sensor is arranged to take a measurement of temperature value averaged over an entire surface of a field of view.

18. A device for inspecting separately conveyed tablets or capsules comprising:

a guide device for guiding the separately conveyed tablets or capsules, which defines a predetermined tablet pathway;

a hotplate, arranged in an area of the guide device;

an IR sensor for detecting radiation in an infrared range arranged opposite the hotplate such that the tablet pathway passes between the hotplate and the IR sensor;

wherein the guide device moves the tablets or capsules relative to the IR sensor during detection by the IR sensor; and an evaluation unit connected to the IR sensor and adapted to compare actual measurement values of the IR sensor with at least one predetermined nominal measurement value.

19. The device of claim 18 wherein the guide device guides the tablets or capsules at a generally uniform conveying speed during detection by the IR sensor.

20. The device of claim 18, wherein an IR-permeable plate is arranged between the hotplate and the tablet pathway to reduce transmission of heat from the hotplate to the tablets or capsules.

* * * * *